United States Patent [19]

Waldrop et al.

[11] 4,007,741
[45] Feb. 15, 1977

[54] TRANSURETHRAL RESECTION APRON SYSTEM

[76] Inventors: Rayburn C. Waldrop, Rte. 3, Box 280, Manor Road, Clinton, Tenn. 37716; Richard G. Brantley, Sparks Road, Knoxville, Tenn. 37921

[22] Filed: Apr. 11, 1975

[21] Appl. No.: 567,428

[52] U.S. Cl. ............................ 128/292; 128/132 R
[51] Int. Cl.² ......................................... A61F 13/16
[58] Field of Search ........... 128/292, 132 R, 132 D; 269/327; 248/95; 232/43.5; 108/25, 26; 2/49–51, DIG. 7

[56] References Cited

UNITED STATES PATENTS

| | | | |
|---|---|---|---|
| 636,462 | 11/1899 | Small | 128/292 |
| 2,457,725 | 12/1948 | Rhowmine | 2/49 A |
| 2,591,783 | 4/1952 | Craddock | 128/132 |
| 3,386,444 | 6/1968 | Brenner et al. | 128/292 |

*Primary Examiner*—Robert W. Michell
*Assistant Examiner*—Henry S. Layton
*Attorney, Agent, or Firm*—Fitch, Even, Tabin & Luedeka

[57] ABSTRACT

A transurethral resection apron system having ties adapted for securing one end of the apron to a urological operating table and the opposite end of the apron about the surgeon's neck, including two generally pentagonal flexible water impervious panels joined along two of their sides to define a capture region for fluids and particles expelled from the bladder during transurethral resections. The apron drains into an outlet in fluid communication with a strainer assembly for filtering out resected particles entrained in the expelled fluids, the fluids passing into a discharge hose for disposal at a remote location. The strainer element may be removed from the strainer assembly and resected particles collected for pathological analysis.

4 Claims, 9 Drawing Figures

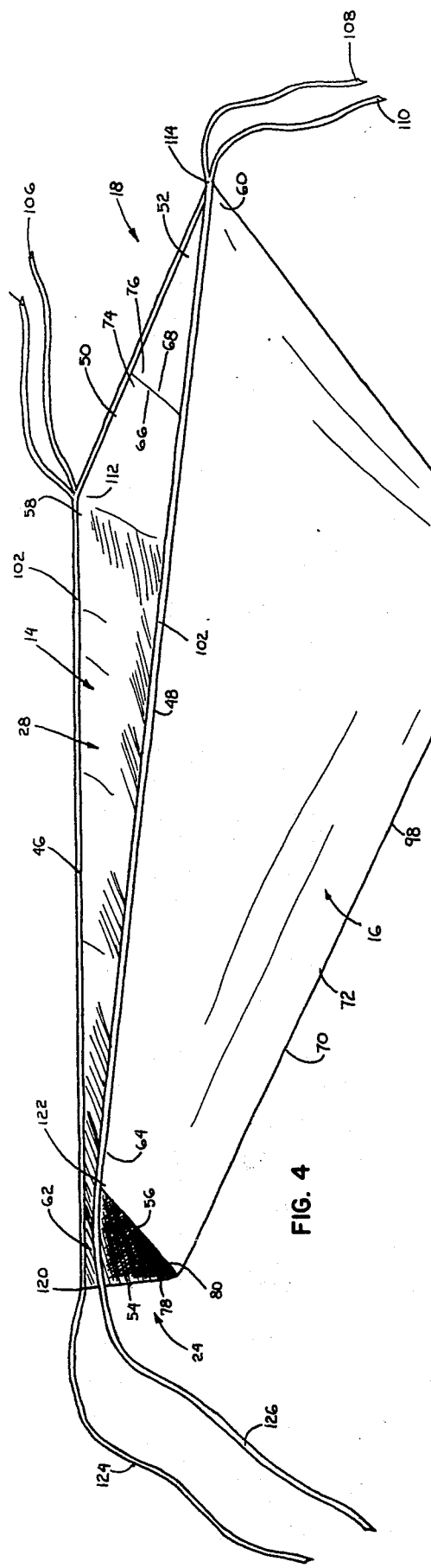

TRANSURETHRAL RESECTION APRON SYSTEM

This invention relates to a transurethral resection apron system for draining of fluids expelled from a patient's bladder and collecting resected particles entrained in the fluids.

In transurethral resections for the removal of bladder and prostate tumors, a hollow rigid sheath adapted for receiving a resectoscope is inserted into the patient's urethra until the end of the sheath is positioned adjacent the area to be resected. A resectoscope in fluid communication with a water and glycine source is passed through the sheath until the cutting end of the resectoscope is positioned adjacent to a prostate gland or bladder tumor. The surgeon then actuates the cutting loop of the resectoscope and as chips are removed from the prostate or bladder tumor, the water-glycine solution flows through the outlet of the resectoscope sheath to irrigate the cutting region. The chips, together with blood and other material are washed through the urethra and into the bladder by this water-glycine solution. When the bladder is filled, the surgeon withdraws the resectoscope whereupon contraction of the bladder muscles purges the bladder of the blood and water-glycine solution together with the resected chips or portions of tumor through the sheath disposed in the patient's urethra.

In the past, the fluids expelled by the patient during transurethral resections have been captured and drained away by manually operated assemblies mounted at one end of a urological operating table. For example, in one prior art system a metal drawer is slidably mounted at one end of the urological table and manually pulled out by the surgeon as fluids are expelled. When the surgeon approaches the table the drawer is manually pushed beneath the table. In another prior art system, a surgical drain bay is attached to a rigid support mounted on the end of a conventional urological operating table. The bay support is pivoted so that when the surgeon pushes against the support, the support and bay collapse. Gravity causes the bay to return to the opened position when the surgeon moves away from the end of the table as fluids are expelled from the bladder. These prior art frame structures restrict the freedom of movement of the surgeon and/or occupy his hand movements. In addition, they detract him from concentrating on the operation at hand during extended operations, such devices also contribute to fatigue of the surgeon. Still further, the prior art systems present less than satisfactory means for collecting resected chips for pathological examinations.

It is therefore an object of this invention to provide a transurethral resection apron system which is adapted for being secured to any conventional urological operating table without the addition of special support means. It is another object of this invention to provide a transurethral resection apron which allows the surgeon's hands to remain free during the resection. It is a further object of this invention to provide a transurethral resection apron system which strains resected chips entrained in fluids expelled by the bladder during the operation. Other objects and advantages of the invention will become apparent by reference to the following description, including the accompanying drawings, in which:

FIG. 3 is a sectional view of the strainer assembly shown in FIG. 1;

FIG. 4 is a perspective view of the apron system shown in FIG. 1 with the strainer assembly shown in an exploded view;

FIG. 5 is a side elevation view of a sleeve adapter shown in FIG. 4;

In accordance with the present disclosure, there is provided a transurethral resection apron system including flexible waterproof apron means defining a fluid capture region adjacent to one end of a urological operating table. The forward end of the apron means is releasably connected to the end of the urological operating table and the rear end of the apron means is releasably connected to the surgeon. Strainer assembly means are mounted in fluid communication with the apron means for draining the fluids captured in the apron. A strainer removably mounted within the strainer assembly collects resected particles entrained in the fluids expelled from the bladder during the resection. Discharge hose means mounted in fluid communication with the strainer assembly is provided for conducting fluids, draining from the apron and passing through the strainer assembly, to a remote depository.

Figure 1:
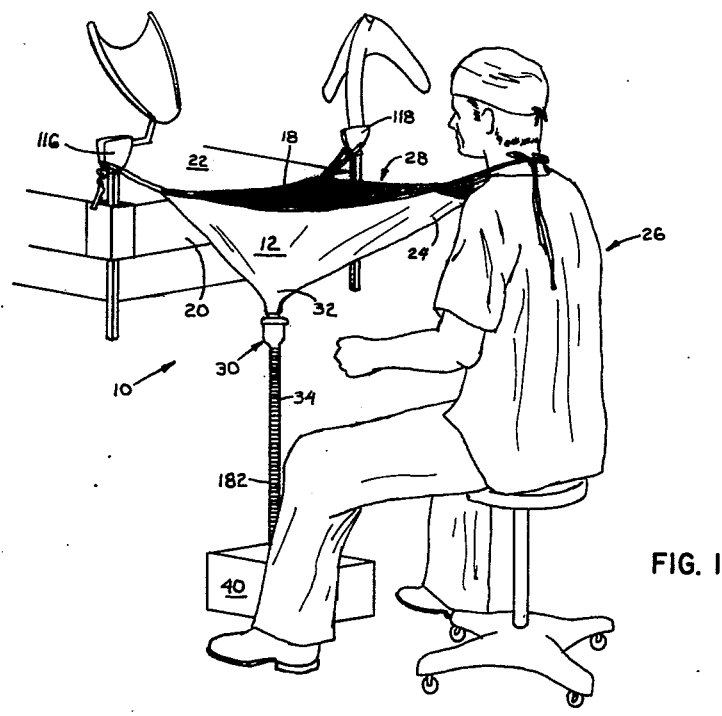
FIG. 1 is a perspective view of a transurethral resection apron system, secured at its forward end to one end of a urological operating table and at its rear end portion to a surgeon, showing various features of the invention.

Referring to the Figures, a transurethral resection (TUR) apron system generally referred to as 10 is shown in FIG. 1. The illustrated TUR apron system includes an apron means 12 having a pair of generally pentagonal panels 14 and 16 joined along two lower sides thereof and diverging upwardly therefrom. The apron means 12 is secured at its forward end 18 to one end 20 of a urological operating table 22 and at its rear end 24 to a surgeon 26 to spread the diverging panels 14 and 16 define a fluid capture region 28 adjacent the pelvic area of a patient in the lithotomy position on the table 22. A strainer assembly 30 is mounted in fluid communication with the apron means 12 adjacent the lower portion 32 of the capture region 28 to receive expelled fluids and other material caught in the apron means 12 and which subsequently drain therefrom. A discharge hose means 34 is mounted in fluid communication with the strainer assembly outlet 36 for conducting the fluids to a remote location, such as a vessel 40. A strainer 42 is removably mounted in the strainer assembly 30 for collecting resected particles entrained in the expelled fluid.

Figure 6:
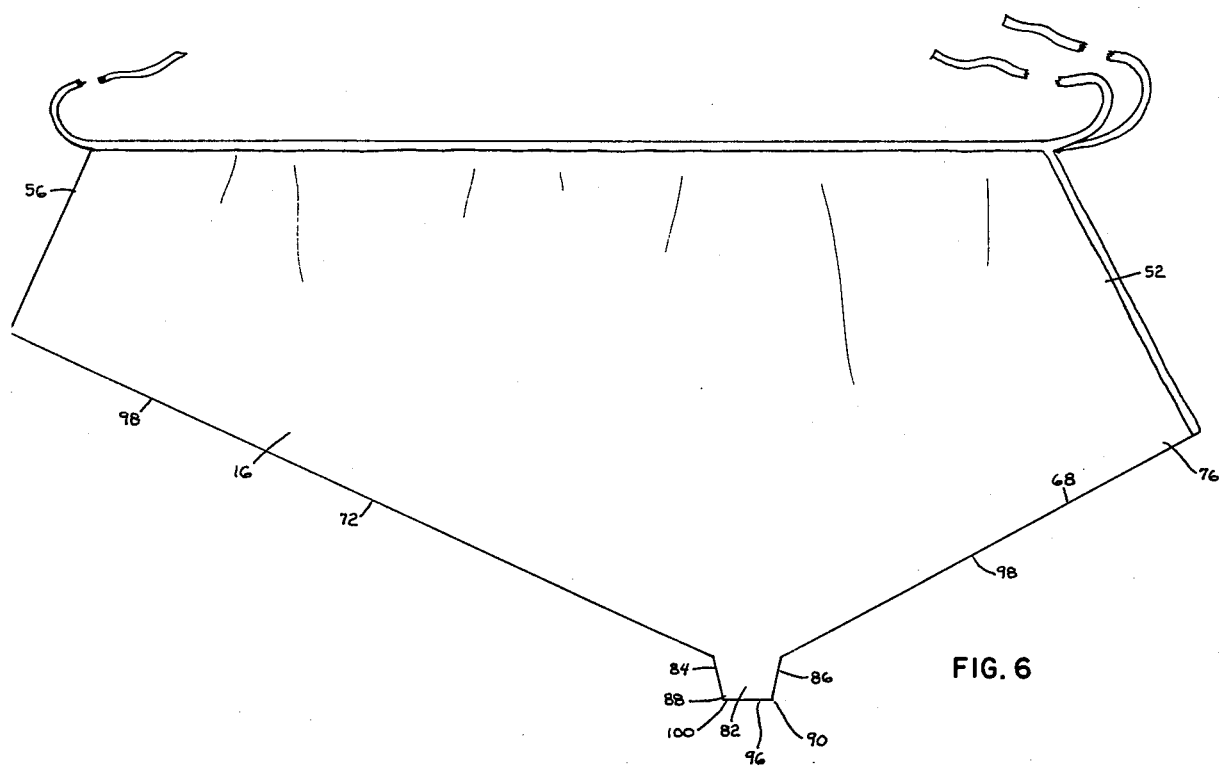
FIG. 6 is a plan view of one of the apron panels shown in FIG. 1.
Figure 7:
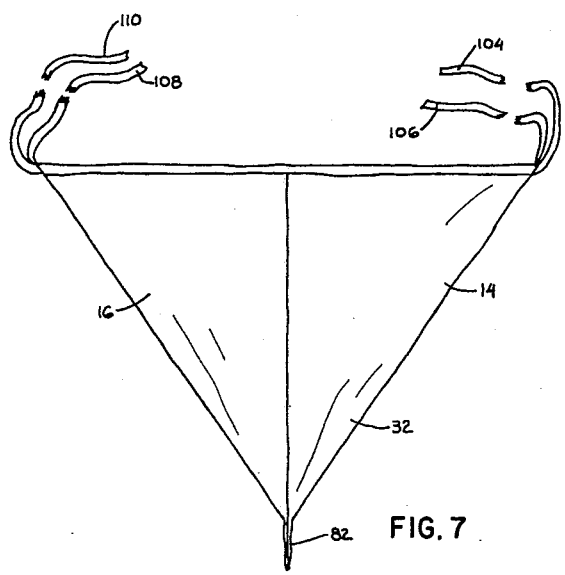
FIG. 7 is a front view of the apron means as shown in FIG. 1.
Figure 8:
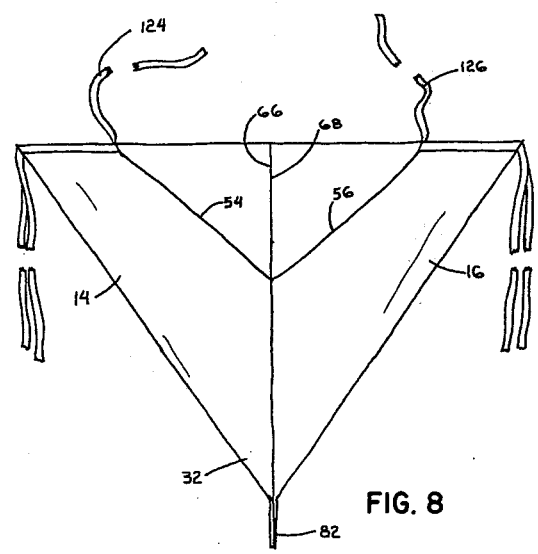
FIG. 8 is a rear view of the apron means as shown in FIG. 1.
Figure 9:
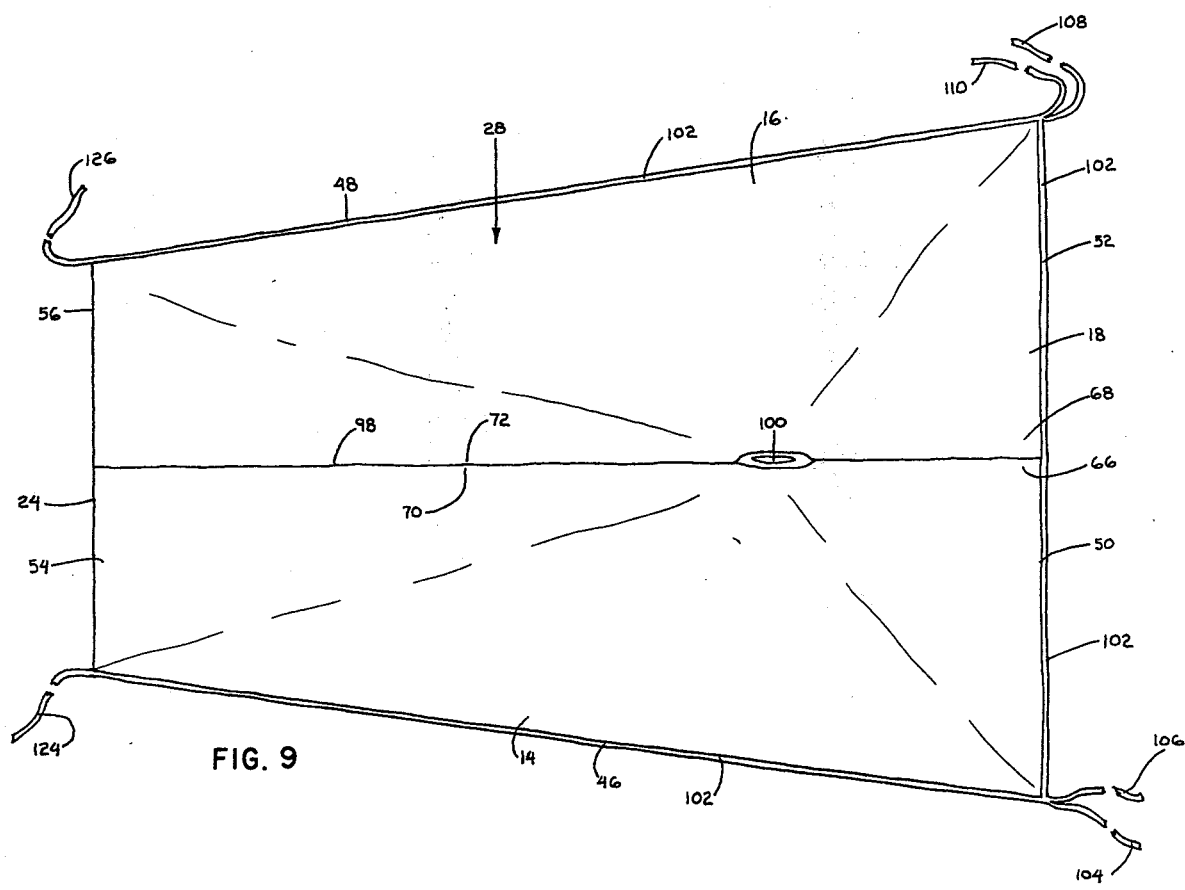
FIG. 9 is a bottom view of the apron means as shown in FIG. 1.

As noted, the apron means 12 defines an elongated fluid capture region 28 adjacent one end 20 of the urological table 22. The illustrated apron means 12 includes two generally pentagonal impervious flexible panels 14 and 16, having upper sides 46 and 48, front sides 50 and 52 and rear sides 54 and 56. The front sides 50 and 52 and the rear sides 54 and 56 form obtuse angles with the opposite ends 58 and 60, and 62 and 64 of the upper sides 46 and 48, respectively. The front sides 50 and 52 and the rear sides 54 and 56 are interconnected by lower forward sides 66 and 68 and lower rear sides 70 and 72. The lower forward sides 66 and 68 extend substantially perpendicularly from the bottom ends 74 (not shown) and 76 of the front sides 50 and 52, respectively. The lower rear sides 70 and 72 extend substantially perpendicularly from the bottom ends 78 and 80 of the rear sides 54 and 56 so that the lower forward sides 66 and 68 and lower rear sides 70 and 72 converge on each other. Each of the panels 14 and 16 in the illustrated embodiment include a truncated tapered panel portions 82 depending from the lower sides of the panels 14 and 16 at the approximate junction of the converging lower sides 66 and 68, and 70 and 72, respectively, as shown in FIGS. 4 and 6. These panel portions 82 include convergent opposite sides 84 and 86 which extend from the lower forward sides 66 and 68 and the lower rear sides 70 and 72, respectively. These sides are interconnected at their lower ends 88 and 90 to the opposite ends of a bottom side 96.

The two panels 14 and 16 are joined along the lower forward sides 66 and 68 and rear sides 70 and 72 to form a water impervious capture region 28. The bond 98 of these sides extends to include the opposite sides 84 and 86, of the corresponding panel portions 82, but does not include the bottom sides 96 of these panel portions thereby causing these partly joined panel portions 82 to define an outlet 100 at the deepest point in the capture region of the apron. The upper sides 46 and 48 and the front sides 50 and 52 of the panels 14 and 16 are reinforced as by bias binding 102 that extends along and is bonded to such sides.

In the illustrated embodiment, the binding 102 is provided with ties 104, 106, 108 and 110 at the junctions 112 and 114 of the upper ends of the front sides 50 and 52 with the forward ends 58 and 60 of the upper sides 46 and 48, respectively, these tips comprising extensions of the binding itself. Referring to FIGS. 1 and 4, the ties 104 and 106 are adapted to be tied about one upright 116 of the urological table 22 and the apron spread open at its front end 18 by pulling the ties 108 and 110 away from the ties 104 and 106. Thereupon, the ties 108 and 110 are tied about the upright 118 of the table 22 to hold the apron in its open position and adjacent the patient disposed on the table. The rear ends 120 and 122 of the upper sides 46 and 48 of the panels 14 and 16 are also provided with ties 124 and 126 adapted to extend around the surgeon's neck and releasably secure the rear end 24 of the apron to the surgeon. With the ends of the apron so anchored, when the surgeon moves away from the table, the apron assumes a funnel-type configuration suitable to catch fluids expelled by the bladder, all without requiring the surgeon to use his hands on the apron. By reason of the flexible nature of the apron, the surgeon is free to move relative to the table within the limits of the apron length dimension thereby enhancing his efficiency.

The outlet 100 is held open and rigidified by a sleeve adapter 128 that extends through the outlet and provides fluid communication between the capture region 28 and a strainer assembly 30. To this end, the illustrated sleeve adapter 128 includes an outwardly flared top portion 130 which is secured as by friction and/or adhesive, in the outlet 100, and a substantially cylindrical bottom portion 132 that depends from the outlet. In the depicted embodiment, a circumferential ridge 133 is provided on the outer surface of the top portion of the sleeve to aid in retarding the flow of fluid between the sleeve adapter and the outlet panel portions. Further, the panel portions 82 are tapered to fit snugly against the flared outer wall of the sleeve adapter 128 to enhance the contact and seal therebetween.

The junction of these top and bottom portions 130 and 132 defines circumferential shoulder 135 about which the bottom sides 96 of the panel portions 82 are wrapped. A plurality of lugs 134 are spaced annularly on the outer wall 136 of the bottom portion of the adapter 128 as shown in FIG. 5, for securing the strainer assembly 30 to the adapter.

Fluids, resected chips or other matter expelled from the bladder, caught in the apron and which flow through the outlet 100 are passed into a strainer assembly 30 in fluid communication with the sleeve adapter 128. The depicted assembly 30 includes a cover 138 having substantially cylindrical neck portion 140 adapted to receive the bottom portion 132 of the sleeve adapter therethrough. The neck portion 140 is releasably connected to the adapter by means of a plurality of dog-legged grooves 142 and 144, each of which includes a vertical portion 146 and a horizontal portion 148 adapted to receive therein the lugs 134 on the adapter 128 in locking relationship. In one embodiment, the horizontal portion 148 of each groove forms an obtuse angle with its vertical portion 146 so that when the sleeve adapter is rotated with respect to the adapter, the lugs in the grooves cause the cover 138 to be urged toward the adapter and cause the upper edge 150 of the neck portion 140 to move into engagement with the circumferential shoulder 135 over which the lower margins of the panel portions 82 extend to aid in sealing against the escape of fluids between the panel portions and the adapter.

The cup-shaped cover 138 is further provided with a downwardly depending cylindrical wall portion 154 adapted to receive therein the top end 156 of the strainer receptacle 158. The receptacle is provided with lugs 160 spaced about its upper margin that are received in dog-legged grooves 162 provided in the wall 154 of the cover so that rotational movement of the receptacle with respect to the cover provides a releasable locking engagement of these two members.

The upper end 156 of the receptacle 158 is further provided with an annular shoulder 168 on the inner wall 170 thereof for receiving a circumferential flange 172 provided on the top and open end 174 of a cup-shaped strainer 42 whose mesh portion 176 nests within the receptacle 158.

As shown in FIG. 3, the strainer 42 mounted within the receptacle serves to collect resected particles entrained in fluids passing through the strainer assembly 30. The illustrated strainer 42 includes a circumferential metallic flange 172 crimped about the upper perimeter of the strainer mesh 176. The strainer 42 preferably is proportioned and dimensioned such that its bottom 178 is spaced apart from the bottom 180 of the receptacle when the strainer is received in the receptacle and so that its circumferential flange 172 fits snugly within the receptacle 158. As fluids pass through the receptacle 158 resected particles are collected in the strainer 42, which is readily removable from the receptacle to gather the collected particles for pathological analysis by merely disconnecting the receptacle from the cover and inverting it to cause the particles to fall out. This ease of particle collection permits periodic collection of particle specimens in the course of an operation without substantial delay or effort.

The receptacle is provided with an inwardly tapered generally cylindrical outlet 36 at its bottom end 180.

A flexible hose 34 is connected at one of its ends to the outlet 36 for conducting fluids passing through the outlet 36 to a remote depository 40. The illustrated hose 34 is flexible and extensible to allow movement of the apron means relative to fixed end 182 of the hose 34 which is in fluid communication with the remote depository 40 shown in FIG. 1. Extensibility of the hose in the depicted embodiment is provided by flutes 184 spaced along the length of the hose.

As noted, during the use of the disclosed system in the course of a transurethral resection, the two pairs of forward ties 104, 106, 108, and 110 are secured to uprights 116 and 118 positioned at the opposite corners of the end of a conventional urological operating table. The reinforced front sides of the joined panels 14 and 16 are thereby stretched into substantial alignment and positioned adjacent the edge of the urological operating table contiguous to the pelvic area of the patient. The rear pair of ties 124 and 126 are tied about the neck of the surgeon so that when he retreats from the table, the apron is pulled taut between the front ties and the surgeon's neck to define an elongated fluid capture area 28 of generally trihedral geometry. As the surgeon approaches the patient to perform the resection, the flexible apron automatically collapses, leaving the surgeon's hands free at all times. When the patient's bladder is filled, the surgeon removes the resectoscope and retreats from the end of the table as fluids are expelled through the sheath in the patient's urethra. The open apron captures the expelled fluids and chips which then drain through the sleeve adapter 128 positioned at the lower apex 188 of the capture area and through the strainer assembly where the chips and other material are caught while the fluids are discharged.

By reason of the elongated nature of the apron, the surgeon is provided with substantial freedom of movement both laterally, vertically and horizontally with respect to the table end. At the same time, with the rear end of the apron tied about his neck, the surgeon's dress is protected from the expelled fluids and he maintains positive control over the opening of the apron without requiring the use of his hands.

Splattering of the expelled fluids is reduced by reason of the sloping walls of the apron. Importantly, splattering is further reduced through the use of a plastic sheet material having a matte finish as the construction material for the apron. One suitable plastic is a polyvinyl chloride film of 8 mil thickness sold by Union Carbide Corporation, New York, N.Y. under the trademark Krene. In addition to the matte finish of this material, it possesses substantial tensile strength combined with substantial stretchability and flexibility. It further has been found not to take a set when folded for storage.

Figure 2:
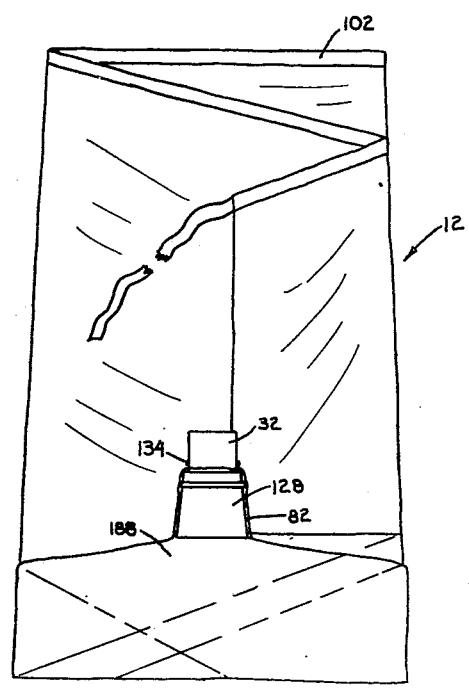
FIG. 2 is a representation of a folded apron means.

The apron 12, with a sleeve adapter 128 fitted therein, is folded for sterilization and storage prior to use as depicted in FIG. 2. As referred to above, the preferred plastic material for the apron does not take a substantial set when folded over extended periods of time, but rather it remains pliable and readily falls open when placed in use. Through the use of relatively inexpensive materials of construction, the apron and its sleeve adapter can be discarded after one use thereby eliminating the time and expense of cleaning, sterilizing, storing, etc. a soiled mechanical apparatus.

While a preferred embodiment has been shown and described, it will be understood that there is no intent to limit the invention by such disclosure, but rather, it is intended to cover all modifications and alternate constructions falling within the spirit and scope of the invention as defined in the appended claims.

What is claimed is:

1. Apparatus for capturing fluids and resected material purged from the bladder of a patient on a urological table during a transurethral resection performed by a surgeon and for separating resected particles entrained in said fluids comprising flexible apron means defining a fluid capture region adjacent one end of said urological table, said apron means including a forward end and a rear end, connecting means adapted for releasably connecting said forward end of said apron to one end of said urological table adjacent to said patient, connecting means adapted for positively and releasably connecting said rear end of said apron to the neck region of said surgeon, said apron means being unsupported by external means in the region between its forward end and its rear end and comprising a plurality of flexible pentagonal panels, each of which includes a top edge, a front edge joined to one end of said top edge and forming an obtuse angle therewith, a rear edge joined to the other end of said top edge and forming an obtuse angle therewith, a bottom forward side, and a bottom rear side, said bottom forward and said bottom rear sides being joined to respective ones of said front and bottom rear edges except at the junction of said edges whereby when said apron is pulled taut by reason of a force applied to its opposite ends, said apron opens to form an upwardly opening capture region, receptacle means releasably connected with said apron means and in fluid communication therewith, strainer means removably held in said receptacle means for collecting said resected material entrained in said fluid passing to said receptacle means, and hose means in fluid communication with said receptacle means for conducting fluids from said receptacle to a remote depository.

2. The apparatus of claim 1 wherein each of said panels includes a panel portion depending from the junction of said bottom front and bottom rear sides, said panel portion having opposite sides that taper inwardly toward each other and a bottom side interconnecting the bottom ends of said opposite sides, said opposite sides of each of said panel portions being joined to the corresponding opposite sides of the other of said panel portions to define a passageway through the thickness of said apron means.

3. The apparatus of claim 1 and including a sleeve adapter extending through the thickness of said apron means and defining a drain outlet therefor, said adapter including a portion having an outwardly flared wall engaged by said apron means and sealably securing said adapter in said apron means.

4. The apparatus of claim 3 wherein said adapter includes a further portion having a cylindrical wall and which is joined to said flared wall portion, said portions defining a circumferential shoulder at their joinder, and wherein said apron wall overlies said shoulder.

* * * * *